(12) United States Patent
Chung

(10) Patent No.: US 10,737,255 B2
(45) Date of Patent: Aug. 11, 2020

(54) WATER SOLUBLE HOMOGENEOUS CATALYSTS THAT ARE RECOVERABLE BY PHASE SELECTIVITY AND HOST-GUEST INTERACTIONS

(71) Applicant: Florida State University Research Foundation, Inc., Tallahassee, FL (US)

(72) Inventor: Hoyong Chung, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 16/373,817

(22) Filed: Apr. 3, 2019

(65) Prior Publication Data

US 2019/0270079 A1 Sep. 5, 2019

Related U.S. Application Data

(62) Division of application No. 15/683,033, filed on Aug. 22, 2017, now Pat. No. 10,300,470.

(51) Int. Cl.
*C07C 41/28* (2006.01)
*C07C 41/30* (2006.01)
(Continued)

(52) U.S. Cl.
CPC ......... *B01J 31/2278* (2013.01); *B01J 31/123* (2013.01); *B01J 31/2208* (2013.01); *B01J 31/2273* (2013.01); *B01J 31/4023* (2013.01); *B01J 31/4038* (2013.01); *B01J 35/12* (2013.01); *B01J 38/52* (2013.01); *C07C 29/46* (2013.01); *C07C 29/56* (2013.01); *C07C 41/28* (2013.01); *C07C 41/30* (2013.01); *C07C 67/333* (2013.01); *C07C 209/68* (2013.01); *C07C 209/70* (2013.01); *C07D 207/20* (2013.01); *C07D 209/48* (2013.01); *C07D 211/02* (2013.01); *C07D 211/70* (2013.01); *C07D 223/10* (2013.01); *C07D 307/28* (2013.01); *C07F 15/0046* (2013.01); *C07H 3/06* (2013.01); *C08B 37/0012* (2013.01); *C08B 37/0015* (2013.01); *C08F 132/08* (2013.01);
(Continued)

(58) Field of Classification Search
CPC ... C08F 132/08; C07D 211/70; C07D 209/48; C07D 207/20; C07D 307/28; C07D 233/10; C07D 211/02; C07C 29/56; C07C 29/46; C07C 41/28; C07C 41/30; C07C 209/68; C07C 67/333; C07C 2603/74; C07C 2601/10; C07C 43/196; C07C 43/235; C08B 37/0015; C08B 37/0012; C07H 3/06
USPC .............................................. 526/92
See application file for complete search history.

(56) References Cited

PUBLICATIONS

Hong et al.; "Efficient Removal of Ruthenium Byproducts from Olefin Metathesis Products by Simple Aqueous Extraction"; Organic Letters; vol. 9, pp. 1955-1957; 2007.*

* cited by examiner

*Primary Examiner* — William K Cheung
(74) *Attorney, Agent, or Firm* — Christopher M. Ramsey; GrayRobinson, P.A.

(57) ABSTRACT

A chemical reaction is catalyzed in an organic solvent using a water soluble N-heterocyclic carbene homogeneous catalyst to form a reaction mixture. An aqueous phase in the reaction mixture. A solvent in which the catalyst is insoluble is added to the reaction mixture, causing the catalyst to migrate to the aqueous phase to form a catalyst-laden aqueous phase. The catalyst is extracted from the catalyst-laden aqueous phase.

16 Claims, 9 Drawing Sheets

1

2

3

Related U.S. Application Data

(60) Provisional application No. 62/377,777, filed on Aug. 22, 2016.

(51) Int. Cl.
| | |
|---|---|
| *C07H 3/06* | (2006.01) |
| *B01J 35/12* | (2006.01) |
| *B01J 38/52* | (2006.01) |
| *C07C 29/46* | (2006.01) |
| *C07C 29/56* | (2006.01) |
| *C07C 209/70* | (2006.01) |
| *C07D 207/20* | (2006.01) |
| *C07D 209/48* | (2006.01) |
| *C07D 211/02* | (2006.01) |
| *C07D 211/70* | (2006.01) |
| *C07D 233/10* | (2006.01) |
| *C07D 307/28* | (2006.01) |
| *C08F 132/08* | (2006.01) |
| *B01J 31/22* | (2006.01) |
| *B01J 31/12* | (2006.01) |
| *C07C 67/333* | (2006.01) |
| *C07C 209/68* | (2006.01) |
| *C08B 37/16* | (2006.01) |
| *B01J 31/40* | (2006.01) |
| *C07D 223/10* | (2006.01) |
| *C07F 15/00* | (2006.01) |

(52) U.S. Cl.
CPC .... *B01J 2231/543* (2013.01); *B01J 2531/821* (2013.01); *B01J 2540/10* (2013.01); *B01J 2540/64* (2013.01); *C07C 2601/10* (2017.05); *C07C 2603/74* (2017.05); *Y02P 20/584* (2015.11)

| Entry | Substrate | Product | Catalyst loading | Conversion | [Ru] (ppm)[b] |
|---|---|---|---|---|---|
| 1 |  16 |  17 | 1 mol % | > 95 % | 53 |
| 2[c] |  18 |  19 | 3 mol % | > 95 % | 284 |
| 3[d] |  20 |  21 | 5 mol % | 75 % | - |
| 4[d] |  22 |  23 | 5 mol % | 26 % | - |

| Entry | Substrate | Product | Conversion |
|---|---|---|---|
| 1 |  24 |  25 | 94 %[b] |
| 2 |  26 |  25 | 93 %[c] |

Ring-opening metathesis polymerization in aqueous media in the presence of catalyst 3.

| Entry | Substrate | Product | Conversion | [Ru] (ppm)[b] |
|---|---|---|---|---|
| 1[c] | EtO₂C CO₂C<br>29 | EtO₂C CO₂Et<br>30 | > 95 % | 5.9<br>(104[d], 63[e]) |
| 2[f] | EtO₂C CO₂Et<br>31 | EtO₂C CO₂Et<br>32 | > 95 % | 3.5 |
| 3 | EtO₂C CO₂Et<br>33 | EtO₂C CO₂Et<br>34 | trace | — |
| 4[c] | Ts-N<br>35 | Ts-N<br>36 | > 95 % | 0.14 |
| 5 | Bn-N<br>37 | Bn-N<br>38 | > 95 % | 5.0 |
| 6 | Ph Ph<br>O<br>39 | Ph Ph<br>O<br>40 | > 95 % | 5.3 |

*FIG. 6*

WATER SOLUBLE HOMOGENEOUS CATALYSTS THAT ARE RECOVERABLE BY PHASE SELECTIVITY AND HOST-GUEST INTERACTIONS

This is a divisional of application Ser. No. 15/683,033, filed Aug. 22, 2017 now U.S. Pat. No. 10,300,470, which claims priority from provisional Application No. 62/377,777, filed Aug. 22, 2016. These priority applications are incorporated by reference in their entirety.

FIELD

This relates to the field of catalysis and, more particularly, to recovery of homogeneous catalysts.

BACKGROUND

Homogeneous catalysts are used to catalyze many different chemical reactions and are invaluable tools in organic synthesis. But a major problem with homogeneous catalysts is that they are soluble in the reaction solution. Because they are soluble, they are difficult to recover from the solution after the reaction is completed. Much research has been devoted to recovering spent homogeneous catalysts, but the conventional catalysts and their associated recovery techniques have their drawbacks.

BRIEF SUMMARY

This disclosure describes homogeneous catalysts that are recoverable from solution by being phase selective and through host-guest interactions.

An example of a method embodying this concept includes separating a water soluble N-heterocyclic carbene homogeneous catalyst from a solution by: (a) forming a host-guest compound between the catalyst and an inclusion compound in the solution; and (b) isolating the host-guest compound from the solution.

Another exemplary method includes catalyzing a chemical reaction in an organic solvent using a water soluble N-heterocyclic carbene homogeneous catalyst to form a reaction mixture. An aqueous phase is formed in the reaction mixture. A solvent in which the catalyst is insoluble is added to the reaction mixture causing the catalyst to migrate to the aqueous phase to form a catalyst-laden aqueous phase. The catalyst-laden aqueous phase is extracted from the reaction mixture.

The methods may include the following optional features.

The catalyst may include a polyethylene glycol functional group.

The catalyst may include a transition metal bonded to an N-heterocyclic carbene moiety bonded to a polyethylene glycol functional group.

The catalyst may include a transition metal bonded to an N-heterocyclic carbene moiety bonded to a polyethylene glycol functional group bonded to a terminal adamantyl group.

The solvent in which the catalyst is insoluble may be an ether.

The solvent in which the catalyst is insoluble may be diethyl ether.

The chemical reaction may be an olefin metathesis reaction.

An example of the catalyst composition includes a water soluble homogeneous catalyst including a transition metal complex having an N-heterocyclic carbene ligand with a polyethylene glycol group thereon.

The catalyst may include a terminal adamantyl group bonded to the polyethylene glycol group.

A cyclodextrin may be bound to the catalyst, the catalyst and cyclodextrin forming a host-guest compound.

The catalyst may include the formula

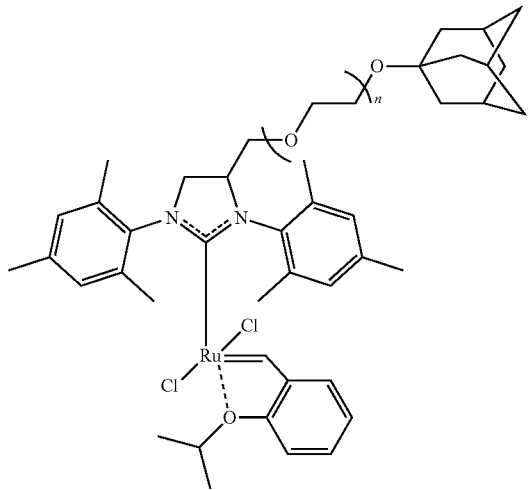

where n is the number of ethylene glycol monomers in the formula.

BRIEF DESCRIPTION OF THE DRAWINGS

FIG. 6 is a table summarizing results of different catalyzed ring closing metathesis reaction in $CH_2Cl_2$. [a]Reactions were carried out at 40° C. with 1 mol % of catalyst 3 in $CH_2Cl_2$ for 1 h. Conversions were determined by $^1H$ NMR spectroscopy. [b]Analyzed by ICP-MS. [c]Reactions were carried out at room temperature. [d]The crude product was diluted with diethyl ether, and then washed with water 5 times. [e]The extracted diethyl ether solution was filtered through silica pluged column. [f]>95% conversion was obtained in 4 h at room temperature.

DETAILED DESCRIPTION OF EXAMPLE EMBODIMENTS

Figure 1:
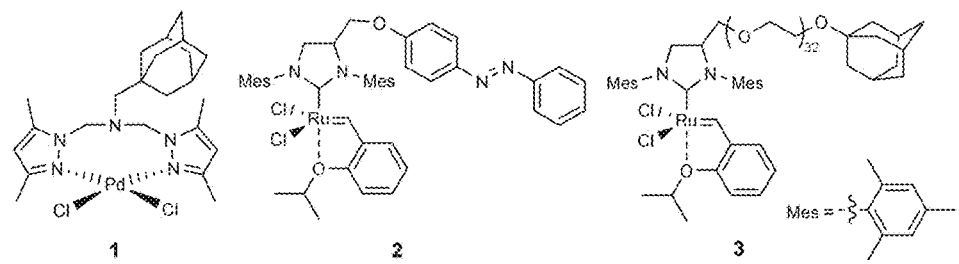
FIG. 1 is a set of catalyst formulas with Compound 3 being an example of the water soluble catalyst.

A homogeneous catalyst is a catalyst that is in the same phase as the reactants. Thus, in a reaction solution the homogeneous catalyst is dissolved. In contrast, a heterogeneous catalyst is a catalyst that is in a different phase than the reactants. In a reaction solution, the heterogeneous catalyst is often a solid. This disclosure relates to homogeneous catalysts and their recovery from the reaction solution.

A host-guest compound may be used in the catalyst recovery process. In general, a host-guest compound includes two or more molecules held together by non-covalent intermolecular forces. The host-guest compound includes an inclusion compound that acts as the host. The inclusion compound has a cavity that receives the catalyst (the guest). The catalyst is held within the cavity by intermolecular forces to form the host-guest compound.

In an example method employing this concept, a water soluble N-heterocyclic carbene homogeneous catalyst is separated from a solution by forming a host-guest compound between the catalyst and an inclusion compound in the solution. The host-guest compound is then isolated from the solution.

The kinetics of the formation of the host-guest compound will vary based on the chemical nature of the inclusion compound and catalyst chosen. Accordingly, an external stimulus such as heat, stirring, ultrasound, or the like may increase the rate of formation of the host-guest compound.

Once formed, the host-guest compound may be insoluble in the solution, which causes it to precipitate. The precipitate may be separated from the solution using a conventional solid-liquid separation technique such as filtration, centrifugation, or the like.

N-heterocyclic carbenes are generally water insoluble. In order to improve the water solubility of the catalyst, a polyethylene glycol group may be bonded to the N-heterocyclic carbene moiety. Advantageously, the catalyst may be soluble in both hydrophobic organic solvents and water.

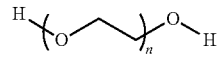

Polyethylene glycol (PEG), which has the general structure shown above is a polymer made from a plurality ethylene glycol monomers. In the formula, n represents the number of ethylene glycol monomers. In general, higher n values are more hydrophilic. Thus the water solubility of the catalyst can be adjusted by choosing a PEG chains with different n. In certain example embodiments n is at least 32.

A polyethylene glycol functional group, as used herein, includes PEG itself and/or PEG derivatives having functionalized ethylene glycol units so long as the PEG functional group renders the catalyst water soluble.

The solution may be an olefin metathesis reaction solution in which an olefin metathesis reaction takes place. N-heterocyclic carbene catalysts are particularly useful for catalyzing these reactions. Other reactions the catalyst may catalyze include, but are not limited to metathesis reactions, Suzuki-Miyaura Coupling, Buchwald-Hartwig Aminations, Negishi Reactions, Hiyama Coupling, Kumada Coupling, Sonogashira Coupling, Heck Reaction, Hydrosilylation, Allene Formation, 1,4-Reduction, Conjugate Addition, Hydrothiolation, Hydroalkoxylation, Hydroamination, Carboxylation & Carbonylation (via Boronic Acids and CH Activation), $CO_2$ Insertion, [3+2] Cycloaddition Reaction (Formation of Triazole), Allylic Substitution, other organocatalytic reactions, among many others. Accordingly, the solution may contain the reactant(s) associated with the reaction being catalyzed and, after the reaction proceeds, the chemical solution may contain the reaction product(s).

Another technique for removing the catalyst from the solution takes advantage of the fact that the catalyst is soluble in water but not in all organic solvents. This functionality allows the catalyst to be removed via phase selectivity.

In this context, another example method includes catalyzing a chemical reaction in an organic solvent using a water soluble N-heterocyclic carbene homogeneous catalyst to form a reaction mixture.

An aqueous phase is formed in the reaction mixture by adding water. The water and organic solvent form distinct phases. Adding to the reaction mixture a solvent in which the catalyst is insoluble causes the water soluble catalyst to migrate to the aqueous phase to form a catalyst-laden aqueous phase. Such a solvent may be, for example, an ether such as diethyl ether. The catalyst-laden aqueous phase may then be extracted from the reaction mixture by separating the two phases. This can be achieved by a conventional phase separation technique such as decanting.

The catalyst may be a transition metal complex organometallic compound has a transition metal bonded to the N-heterocyclic carbene moiety and azobenzene moiety. The transition metal may be a transition metal that functions as a catalyst. Examples of such transition metals include Ru, Pd, Ni, Cu, Fe, Ag, Au, Rh, Ir, Ni, Pd, and Cu among others.

A particular example of the catalyst includes the formula shown below.

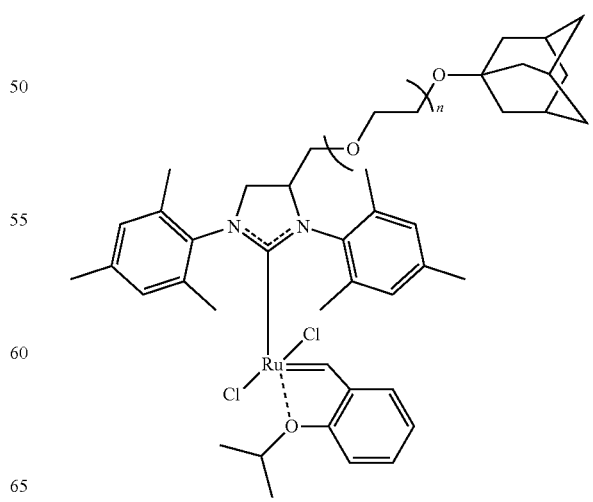

In this formula, n is the number of ethylene glycol monomers.

The inclusion compound may be any conventional inclusion compound used in host-guest chemistry, such as, for example, cyclodextrins, porphyrins, calixarenes, cucurbiturils, and crown ethers among others.

In certain examples a cyclodextrin is used as the inclusion compound with a catalyst having a terminal adamantyl group bound to the PEG functional group. The adamantyl group interacts with the cyclodextrin to provide the host-guest interaction necessary to form the host-guest compound. The adamantly group includes an adamantane backbone. The adamantane backbone may be functionalized if desired to modulate its properties.

Cyclodextrins are oligosaccharides including a plurality of sugar molecules linked together to form a ring. Examples include, but are not limited to alpha-cyclodextrin, beta-cyclodextrin, and gamma-cyclodextrin. The cyclodextrin backbone may be functionalized as desired to modify its properties. For example, it may be modified with functional groups that modify the interaction with a particular catalyst.

The inclusion compound may be functionalized in such a way that it binds to a solid substrate surface such as a metal surface, a magnetic surface, a silica surface or the like. By attaching the inclusion compound to a surface, the inclusion compound becomes immobilized, which may make removing the inclusion compound from solution easier.

In a particular example, the solid substrate is silica such as activated silica. The surface of the silica is functionalized with an isothiocyanate. The isothiocyanate portion acts as a bonding point for amines. Accordingly, if the inclusion compound is functionalized with a terminal amine group, it can be attached to the silica via the isothiocyanate group.

Silica is a porous material and may be used in particle form. Examples of sizes of silica particles include 50 to 300 mesh, 60 to 270 mesh, or 70 to 230 mesh. Examples of pore sizes include 10 to 200 Å, 30 to 150 Å, 20 to 80 Å, or about 60 Å.

EXAMPLES

This section discusses particular examples of the composition and methods for illustrative purposes. The scope of the claims is not limited to the details discussed in this section.
Synthesis of Catalyst Compound 3

Figure 2:
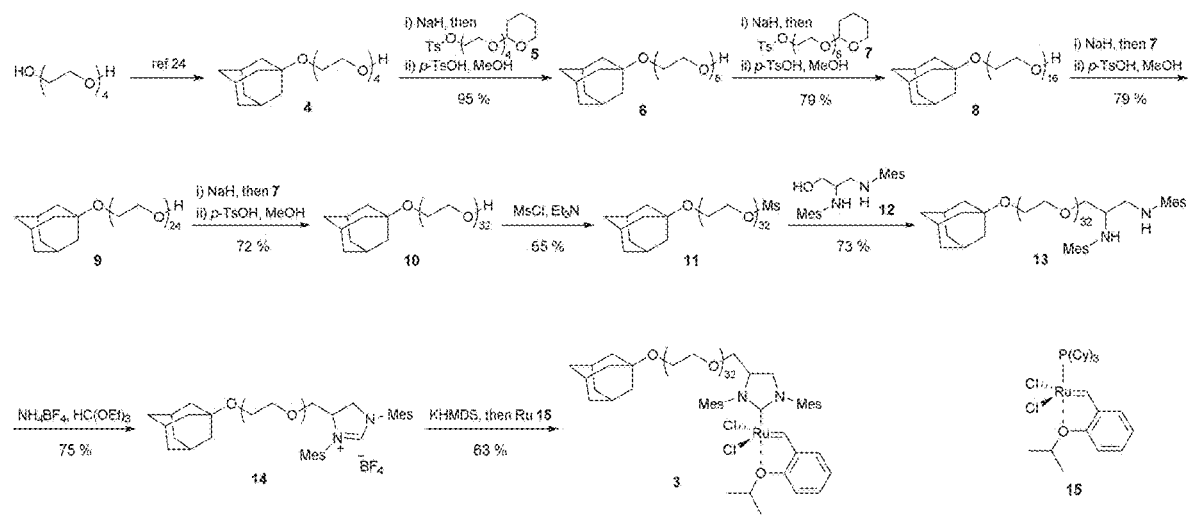
FIG. 2 is a reaction scheme of an example method of making Compound 3.

FIG. 1 displays three catalyst structures that utilize host-guest interactions for the recovery of organometallic catalysts. Compound 1 contains an adamantyl tether for the recovery of Pd catalyst following Suzuki-Miyaura coupling. Compound 2 is a Ru-based catalyst recoverable using host-guest interactions. Compound 3 is an example of the homogeneous catalyst described in this disclosure, which is reactive in aqueous solution with excellent recovery rates of catalysts (0.14 ppm Ru residue in $CH_2Cl_2$ and 53 ppm in water). FIG. 2 summarizes an example of a method of synthesizing Compound 3.

Compound 3 was prepared with tetraethylene glycol. Tetraethylene glycol was converted into the adamantyl tethered tetraethylene glycol (Compound 4). Separately, tetrahydropyranyl (THP) ether protected ethylene glycol extending units (Compound 5, Compound 7) were also synthesized from tetraethylene glycol. The number of ethylene glycol repeating units were increased sequentially through iterative substitution reactions between tosylated ethylene glycol and alcohols of another ethylene glycol compound. As the main purpose of ethylene glycol is water solubility, 32 repeating units was determined to be an effective example to efficiently dissolve the ligand and achieve this goal.

Finally, a 32 ethylene glycol repeating unit containing methanesulfonate (Compound 11) was generated from Compound 10 with methanesulfonyl chloride and triethylamine. Diamine Compound 13 was synthesized using a substitution reaction between Compound 11 and N,N'-dimesityl-2,3-diamino-1-propanol (Compound 12). The reaction of the resulting diamine (Compound 13) with triethyl orthoformate and ammonium tetrfluoroborate yielded imidazolium salt (Compound 14). In situ generation of the carbene of Compound 14 with potassium bis(trimethylsilyl)amide (KHMDS), followed by the addition of Hoveyda-Grubbs 1$^{st}$ generation catalyst (Compound 15) generated the desired catalyst (Compound 3).

Additional details of this reaction scheme follow.

Synthesis of Compound 6

To a stirred solution of sodium hydride (60 wt % in mineral oil, 497 mg, 12.4 mmol, 1.5 equiv.) in THF (20 mL) at 0° C., Compound 4 (2.72 g, 8.28 mmol, 1.0 equiv.) in THF (10 mL) was slowly added. The resulting mixture was stirred for 30 min, Compound 5 (4.30 g, 9.94 mmol, 1.2 equiv.) in THF (10 mL) was added. The reaction mixture was stirred for 5 h at room temperature. After the desired reaction time, a few drops of water were added to quench the reaction. The reaction mixture was filtered through Celite to remove unwanted solid residue. The organic solution was dried over anhydrous MgSO4 and evaporated under the reduced pressure. The residue was purified by flash column chromatography on silica gel (eluted with EtOAc/MeOH=15/1) to give the THP-protected Compound 6 as a pale yellow oil.

A chemical, p-TsOH.$H_2O$ (100 mg, 0.526 mmol) was added to the MeOH (50 mL) solution of THP-protected compound that is synthesized from the previous step. The reaction mixture was stirred overnight at room temperature. Triethyl amine (1.0 mL) was added to quench the p-TsOH, and then the mixture was filtered through Celite. The organic solution was dried over anhydrous $MgSO_4$ and evaporated under reduced pressure. The synthesized Compound 6 was 3.98 g (7.89 mmol, 95.3% in two-step yield) and it was obtained as a pale yellow oil.

Synthesis of Compound 7

Figure 7:
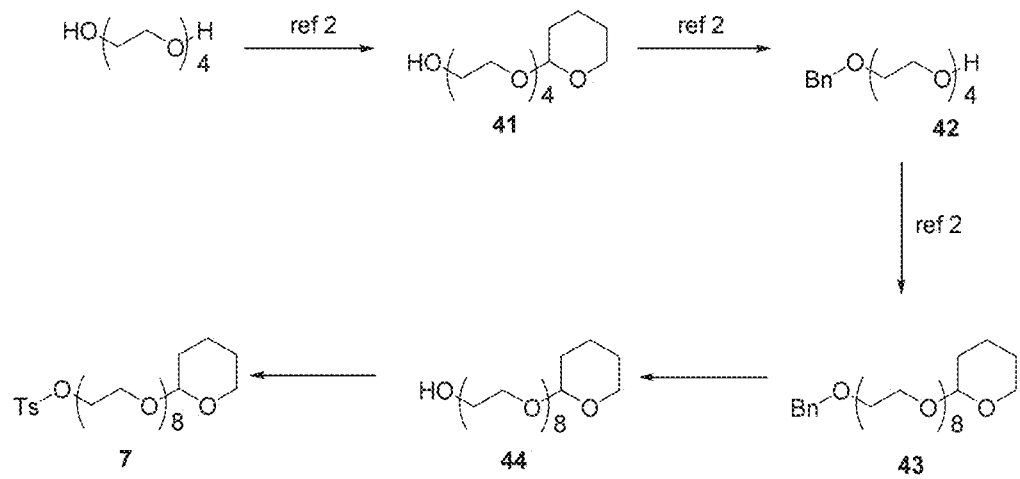
FIG. 7 is a reaction scheme for making Compound 7.

Referring to FIG. 7, to a stirred solution of Compound 43 (28.23 g, 51.8 mmol) in EtOAc (250 mL) at room temperature, Pd/C (10 wt %, 300 mg) was added. The resulting mixture was stirred overnight at reflux under an $H_2$ balloon. Upon cooling to room temperature, the Pd/C was filtered through Celite to remove unwanted solid residue. The organic solution was dried over anhydrous $MgSO_4$ and evaporated under the reduced pressure. The produced Compound 44 was 23.55 g (51.8 mmol, 100%) and it was obtained as a colorless oil.

To a stirred solution of Compound 44 (23.55 g, 51.8 mmol, 1.0 equiv.) in $CH_2Cl_2$ (300 mL), triethylamine (18.1 mL, 130 mmol, 2.5 equiv.) was added. Then, p-toluenylsulfonyl chloride (TsCl, 11.86 g, 62.2 mmol, 1.2 equiv.) was added to the reaction solution at 0° C. The reaction mixture was warmed to room temperature and stirred for 5 h. The reaction mixture was extracted with $CH_2Cl_2$ (200 mL×3). The organic solution was dried over anhydrous $MgSO_4$ and evaporated under the reduced pressure. The residue was purified by flash column chromatography on silica gel (eluted with EtOAc/MeOH=20/1) to give Compound 7 (23.83 g, 39.1 mmol, 75.6%) as a pale yellow oil.

Synthesis of Compound 8

Figure 8:
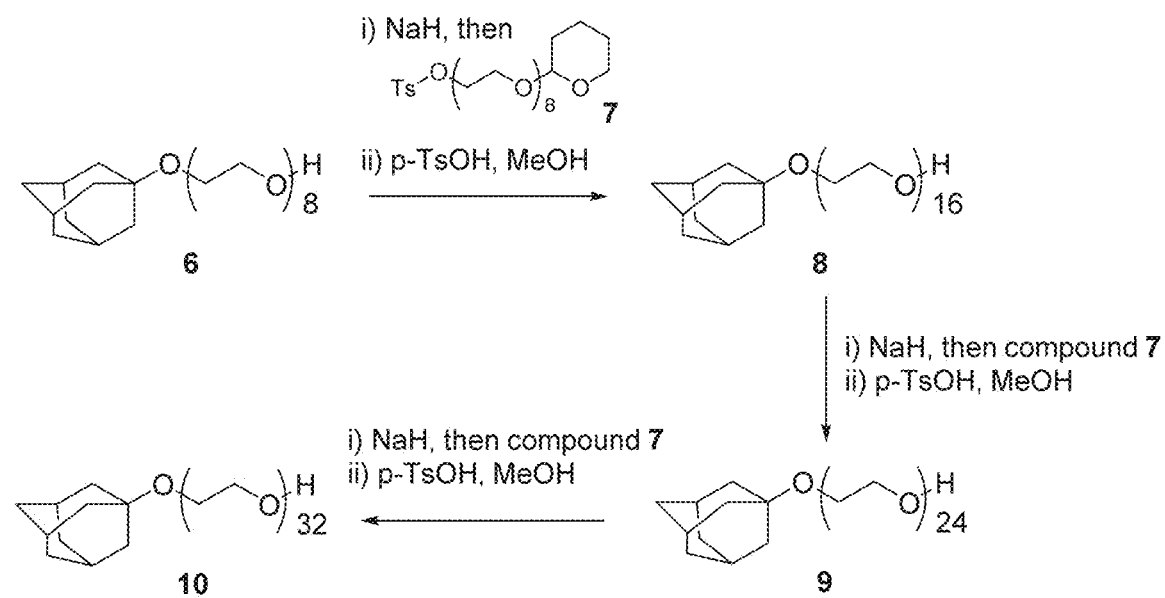
FIG. 8 is a reaction scheme for making Compound 10.

Referring to FIG. 8, using the procedure for Compound 6, a mixture of Compound 6 (3.98 g, 7.89 mmol, 1.0 equiv.), NaH (60 wt % in mineral oil, 473 mg, 11.8 mmol, 1.5 equiv.), and Compound 7 (5.76 g, 9.47 mmol, 1.2 equiv.) in THF (50 mL) was reacted to give the THP-protected Compound 8.

The THP-protected Compound 8 was deprotected with p-TsOH.$H_2O$ (100 mg, 0.526 mmol) in MeOH (50 mL). The Compound 8 was obtained in 78.7% yield (two-step yield, 5.32 g, 6.21 mmol) as a colorless oil.

Synthesis of Compound 9

Using the procedure for Compound 6, a mixture of Compound 8 (5.32 g, 6.21 mmol, 1.0 equiv.), NaH (60 wt % in mineral oil, 373 mg, 9.32 mmol, 1.5 equiv.), and Compound 7 (4.54 g, 7.45 mmol, 1.2 equiv.) in THF (50 mL) was reacted to give the THP-protected Compound 9.

The THP-protected Compound 9 was deprotected with p-TsOH.H2O (100 mg, 0.526 mmol) in MeOH (50 mL). Compound 9 was obtained in 78.7% yield (two-step yield, 5.91 g, 4.89 mmol) as a colorless oil.

Synthesis of Compound 10

Using the procedure for Compound 6, a mixture of Compound 9 (5.91 g, 4.89 mmol, 1.0 equiv.), NaH (60 wt % in mineral oil, 294 mg, 7.34 mmol, 1.5 equiv.), and Compound 7 (3.42 g, 5.62 mmol, 1.2 equiv.) in THF (50 mL) was reacted to give the THP-protected Compound 10.

The THP-protected Compound 10 was deprotected with p-TsOH.$H_2O$ (100 mg, 0.526 mmol) in MeOH (50 mL). The Compound 10 was obtained in 71.5% yield (two-step yield, 5.46 g, 3.50 mmol) as a white solid.

Synthesis of Compound 11

Figure 9:
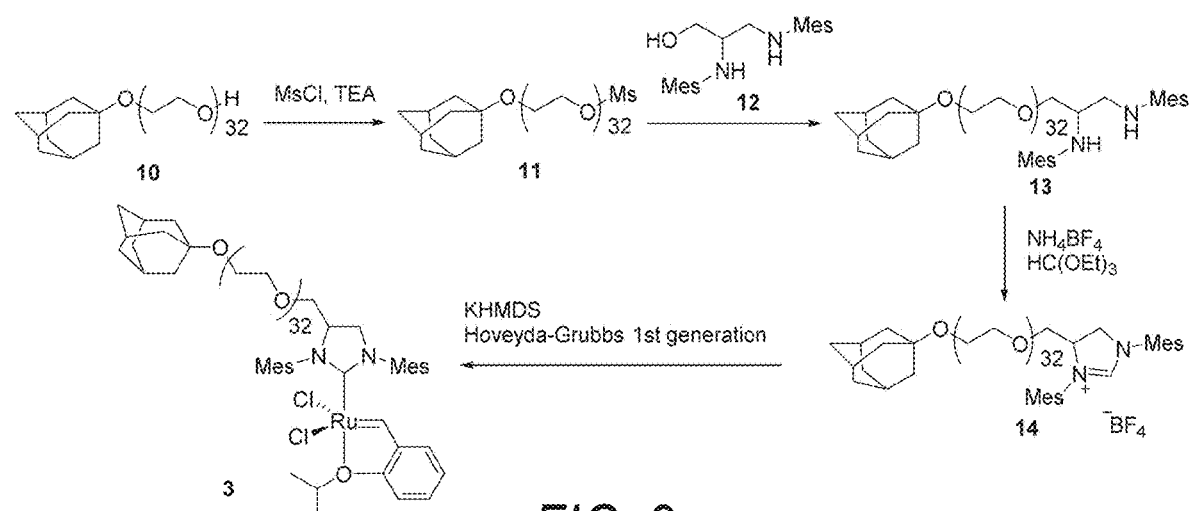
FIG. 9 is a reaction scheme for making Compound 3.

Referring to FIG. 9, to a stirred solution of Compound 10 (1.56 g, 1.00 mmol, 1.0 equiv.) in $CH_2Cl_2$ (10 mL), triethylamine (0.35 mL, 2.50 mmol, 2.5 equiv.) was added. Then, methanesulfonyl chloride (MsCl, 0.12 mL, 1.50 mmol, 1.5 equiv.) was added to the reaction solution at 0° C. The reaction mixture was warmed to room temperature and stirred for overnight. The reaction mixture was filtered through Celite. The organic solution was dried over anhydrous $MgSO_4$ and evaporated under the reduced pressure. The residue was purified by flash column chromatography on silica gel (eluted with EtOAc/MeOH=1/2) to give Compound 11 (1.07 g, 0.652 mmol, 65.2%) as a pale yellow oil.

Synthesis of Compound 13

To a stirred solution of sodium hydride (60 wt % in mineral oil, 51.0 mg, 1.28 mmol, 2.0 equiv.) in THF (5 mL) at 0° C., Compound 12 (460 mg, 1.41 mmol, 2.2 equiv.) in THF (2 mL) was slowly added. The resulting mixture was stirred for 30 min, Compound 11 (1.05 g, 0.64 mmol, 1.0 equiv.) in THF (3 mL) was added. The reaction mixture was stirred for overnight at room temperature. A few drops of water were added to quench the reaction. The mixture was filter through Celite. The organic solution was dried over anhydrous $MgSO_4$ and evaporated under the reduced pressure. The residue was purified by flash column chromatography on silica gel (eluted with EtOAc/MeOH=1/1) to give the Compound 13 (0.87 g, 0.47 mmol, 73.4%) as a pale yellow oil.

Synthesis of Compound 14

To a stirred solution of Compound 13 (869 mg, 0.465 mmol, 1.0 equiv.) in triethylorthoformate (7 mL), ammonium tetrafluoroborate (53.6 mg, 0.512 mmo. 1.1 equiv.) was added. The reaction mixture was stirred for 12 h at 120° C. Upon cooling to room temperature, the product was precipitated from ether. The precipitate was collected by centrifuge. The final product, Compound 14, was 867 mg (0.349 mmol, 75.0%) and it was a sticky yellow oil.

Synthesis of Compound 3

In a glove box, Compound 14 (120 mg, 0.061 mmol, 1.0 equiv.) and potassium bis(trimethylsilyl)amide (KHMDS, 18 mg, 0.092 mmol, 1.5 equiv.) were dissolved in toluene (3 mL) and added to a solution of Hoveyda-Grubbs $1^{st}$ generation (55 mg, 0.092 mmol, 1.5 equiv.) in toluene, then the solution was transferred to a flask. The sealed flask was removed from a glove box and stirred for 3 h at 80° C. The resulting solution was purified by flash column chromatography on neutral alumina (Brockmann activity I, eluted with EtOAc/MeOH=15/1) to give Compound 3 (84.6 mg, 0.0384 mmol, 63.0%) as a sticky dark green oil.

Synthesis of a Silica-Grafted β-Cyclodextrin Host Compound

Synthesis of 1-(p-Toluenesulfonyl)imidazole

Figure 10:
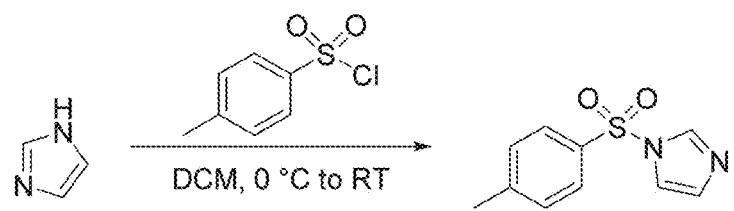
FIG. 10 is a reaction scheme for making 1-(p-Toluenesulfonyl)imidazole.

Referring to FIG. 10, a 1 L, 3-necked round-bottom flask was fitted with a nitrogen inlet adapter, a pressure-equalizing addition funnel, a thermometer, and a stir bar. This flask was charged with imidazole (65 g, 954.7 mmol, 2.2 equiv.) in 250 mL dry dichloromethane and cooled to 0° C. The addition funnel was charged with a solution of p-toluenesulfonyl chloride (80 g, 419.6 mmol, 1 equiv.) in another 250 mL dry dichloromethane (0.84 M in total DCM).

This solution was added dropwise at 0° C. over 1.5 hours, then warmed to room temperature and stirred for a further 2.5 hours. The reaction was filtered through a pad of silica with 500 mL of a 1:1 hexanes:EtOAc solution. The filtrate was concentrated under reduced pressure to give an off-white solid which was dissolved in 50 mL of ethyl acetate then crashed out into 500 mL of hexanes. 1-(p-Toluenesulfonyl)imidazole was collected by filtration as a white, crystalline solid. (79 g, 0.3556 mol, 85% yield).

Synthesis of mono(6-p-toluenesulfonyl-6-deoxy)-β-cyclodextrin (Compound 45)

Figure 11:
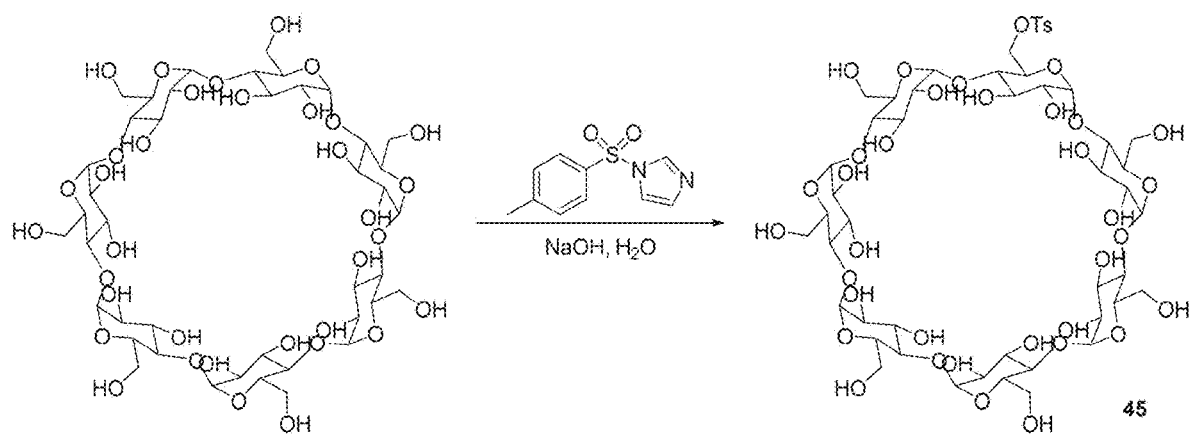
FIG. 11 is a reaction scheme for making Compound 45.

Referring to FIG. 11, A 1 L round-bottom flask, with no special precaution against air or moisture, was charged with β-cyclodextrin (20 g, 17.6 mmol, 1 equiv.) and 450 mL deionized water. The mixture was heated at 60° C. with vigorous stirring until the solution became clear, then cooled to room temperature. 1-(p-Toluenesulfonyl)imidazole (15.7 g, 70.5 mmol, 4 equiv.) was ground to a fine powder by mortar and pestle before adding to the clear reaction solution all at once. The reaction was stirred for 2.5 hours at room temperature.

After the required time, the reaction mixture was charged with a solution of sodium hydroxide (9 g in 25 mL water, cooled completely to room temperature before addition) over 10 minutes via addition funnel. This reaction mixture was stirred for no more than 15 minutes after addition of base before being filtered through a glass frit to remove unreacted imidazole reagent. The filtrate was quenched by the addition of 24.1 g of ammonium chloride, which was allowed to completely dissolve before continuing.

The reaction mixture was concentrated by blowing a gentle stream of air over the flask overnight. Compound 46 began to precipitate almost immediately. The following morning, the reaction volume had been reduced by half and the solid product was collected by vacuum filtration and washed twice with 100 mL ice-cold water, and once with 200 mL acetone.

The collected product contained a large amount of hydrolyzed impurity which was inseparable from the desired product and therefore carried on into the next reaction where it could be easily removed. Yield is approximately 45%.

Synthesis of mono-(6-azido-6-deoxy)-β-cyclodextrin (Compound 46)

Figure 12:
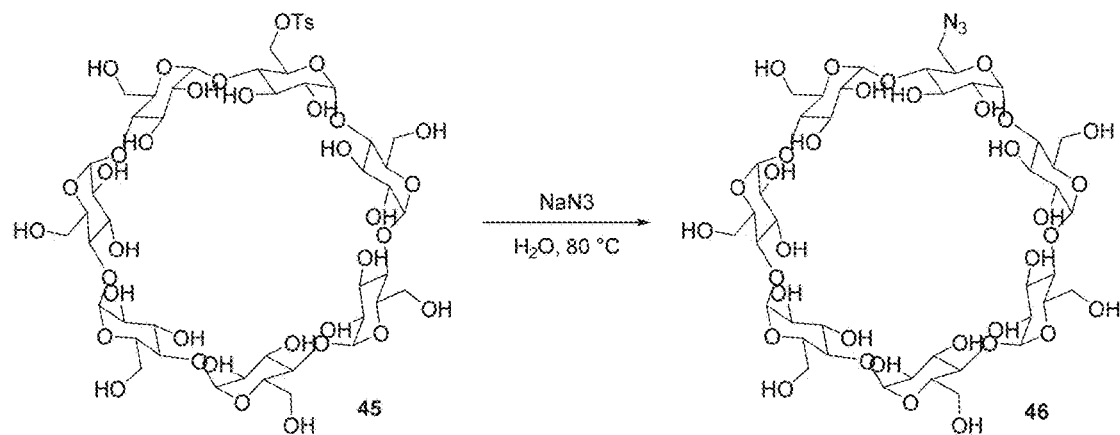
FIG. 12 is a reaction scheme for making Compound 46.

Referring to FIG. 12, sodium azide (2.81 g, 43.2 mmol, 5 equiv.) was added to a solution of mono-(6-p-toluenesulfonyl-6-deoxy)-3-cyclodextrin (Compound 46) (11.1 g, 8.64 mmol, 1 equiv.) in 108 mL (0.08 M) of deionized water in a 250 mL round-bottom flask, with no special precautions taken against air. This reaction mixture was stirred for 12 hours at 80° C.

The reaction mixture was then filtered through a fritted funnel while hot to remove hydrolyzed material from the previous reaction (insoluble in water), and the clear filtrate was added to 300 mL of acetone, causing a white solid to crash out of solution. This solid was collected by vacuum filtration and washed twice with 100 mL portions of acetone to yield 8.09 g of Compound 47 as a white powder. (6.97 mmol, 40% yield over 2 steps from 3-cyclodextrin).

Synthesis of mono-(6-amino-6-deoxy)-3-cyclodextrin (Compound 47)

Figure 13:
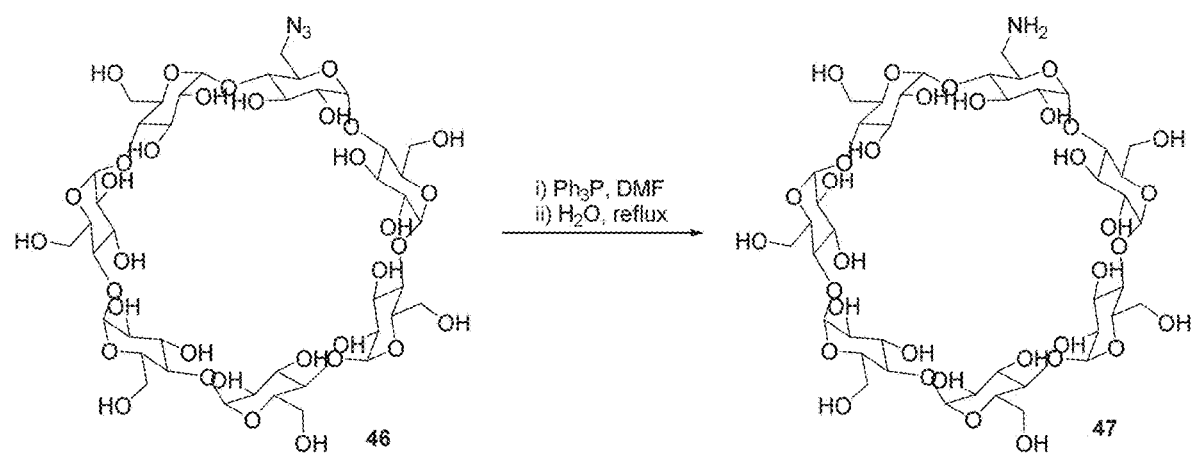
FIG. 13 is a reaction scheme for making Compound 47.

Referring to FIG. 13, triphenyl phosphine (1.90 g, 7.24 mmol, 1.1 equiv.) was added to a solution of mono-(6-azido-6-deoxy)-3-cyclodextrin (Compound 47) (7 g, 6.03 mmol, 1 equiv.) in DMF (12 mL, 0.5 M) in a 100 mL oven-dried round-bottom flask equipped with a stir bar and condenser. This reaction was stirred at room temperature for 2 hours before charging with 1 mL of water and heating the reaction to reflux for a further 3 hours.

After 3 hours had passed, the reaction was cooled to room temperature and diluted with acetone (~70 mL), causing a white precipitate to quickly form. This precipitate was collected by vacuum filtration and washed five times with cold acetone. The resulting white solid was dried thoroughly in a vacuum oven for 6 hours at 65° C. to yield 6.09 g of Compound 48 (90% yield).

Triethoxy(3-isothiocyanatopropyl)silane (Compound 48)

Figure 14:
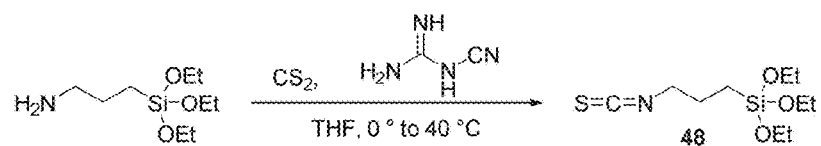
FIG. 14 is a reaction scheme for making Compound 48.

Referring to FIG. 14, a 250 mL round-bottom flask was charged with 3-aminopropyltriethoxysilane (7 mL, 30 mmol, 1 equiv.) and 20 mL anhydrous THF and cooled to 0° C. in an ice-water bath. Carbon disulfide (2.7 mL, 44.8 mmol, 1.5 equiv.) was added dropwise over 20 minutes via syringe pump, and the reaction was stirred at 0° C. for 3 hours before warming to room temperature. Dicyandiamide (3.8 g, 44.8 mmol, 1.5 equiv.) was then added in one portion, along with an additional 20 mL anhydrous THF (0.75 M total) and 3 drops of triethylamine. This mixture was heated at 40° C. for 3 hours before the volatiles were removed in vacuo.

The resulting residue was extracted with diethyl ether several times, the combined organic layers were washed twice with a small amount of water, then dried and concentrated. The resulting crude product was purified by Kügelrohr distillation (120° at 1.5 Torr) to yield 3.86 g of Compound 49 as a clear yellow liquid (14.7 mmol, 49% yield).

Synthesis of silica-grafted isothiocyanate derivative (Compound 49)

Figure 15:
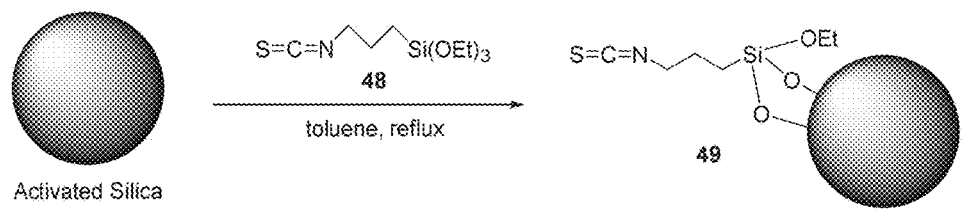
FIG. 15 is a reaction scheme for making Compound 49.

Referring to FIG. 15, silica gel (70-230 mesh, 60 Å pore size, 550 m$^2$/g) was activated by stirring in 50:50 $HNO_3$ (70%):$H_2O$ at reflux for 24 hours. The newly activated silica was collected by vacuum filtration and washed several times with water, then methanol. The silica was then collected and dried in a vacuum oven at 100° C. overnight, and stored in an air-free environment prior to use.

Activated silica (5 g) was dispersed in toluene (50 mL) with vigorous stirring for 5 minutes before being charged with isothiocyanate (Compound 49) (3 grams, 11.4 mmol). This mixture was heated at reflux for 24 hours with gentle stirring before being cooled to room temperature. The cooled mixture was collected by filtration and washed several times with toluene before being dried in a vacuum oven at 60° C. for 16 hours. This product was carried on immediately without further purification.

Figure 16:
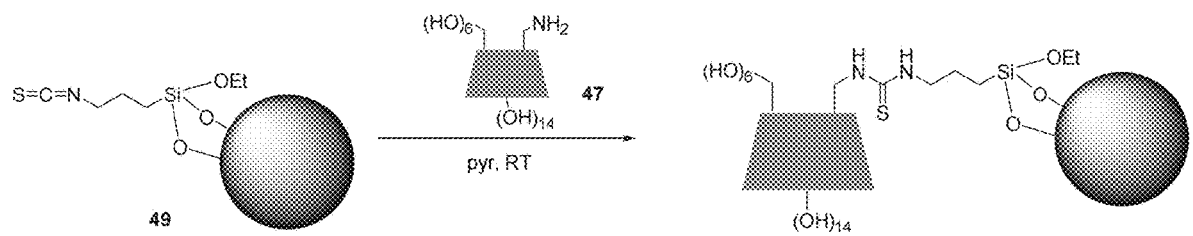
FIG. 16 is a reaction scheme for making an example inclusion compound bound to silica.

Synthesis of the Silica-Grafted β-Cyclodextrin and its TGA Analysis β-Cyclodextrin Host Compound Referring to FIG. 16, a large excess of mono-(6-amino-6-deoxy)-3-cyclodextrin (Compound 47) (8 g, 7.05 mmol) was charged to a 50 mL oven-dried round-bottom flask and dissolved in a minimum amount of pyridine (~5 mL). This solution was charged with silica-grafted isothiocyanate derivative Compound 49 (5.50 g) and stirred at room temperature for 24 hours.

The resulting slurry was vacuum filtered, and the recovered silica derivative was washed several times with water before drying in a vacuum oven for 16 hours at 75° C.

Thermogravimetric analysis (TGA) was applied to the host compound in an effort to quantify the degree of functionalization of the surface of the silica gel with 3-cyclodextrin. Silica gel itself shows a loss of about 5% before 200° C., likely due to the presence of adsorbed water on the surface of the silica. A further 6% of weight loss is attributed to the dehydration of surface hydroxyl groups on silica. The host compound shows water loss at about 3-4% before dropping sharply in weight between 220 and 600° C. This steep drop in weight is expected due to the thermal decomposition of 3-cyclodextrin moieties. This provides a direct evidence of the grafting of 3-cyclodextrin units onto the silica gel, with a concentration of $1.57 \times 10^{-4}$ mmol/mg of 3-cyclodextrin grafted to silica.

Catalyzed Reactions Using Compound 3

Figure 17:
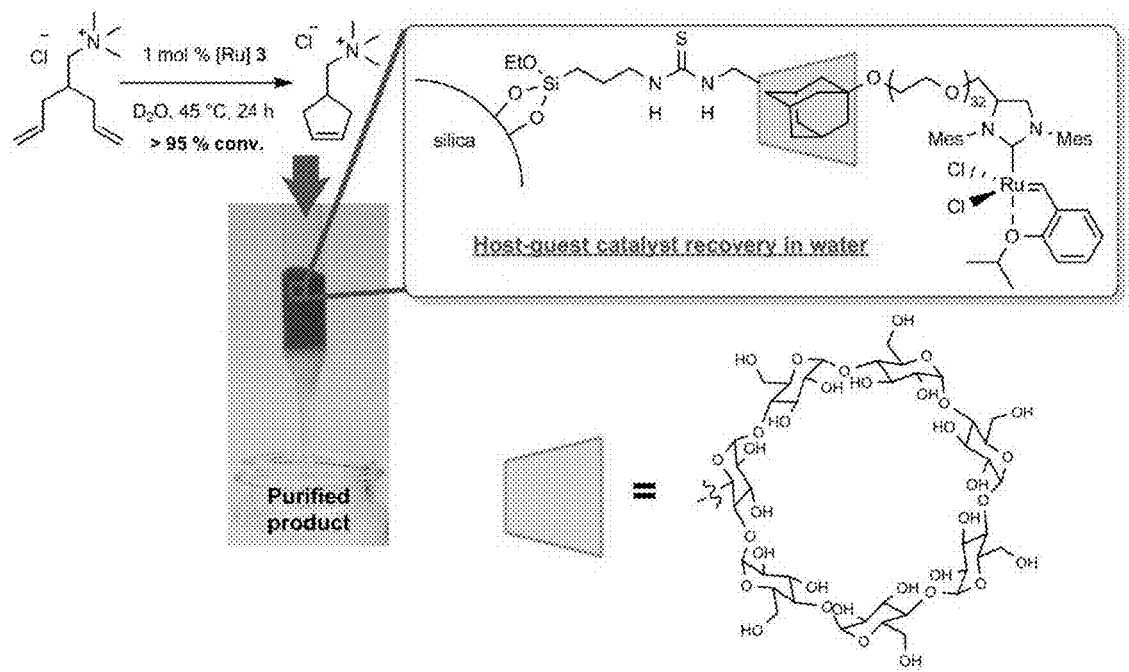
FIG. 17 is an illustration of an olefin metathesis reaction and using host-guest interactions to recover the catalyst.

FIG. 17 illustrates an example of Ru-catalyzed metathesis and catalyst recovery in aqueous media via host-guest interactions. First, a homogenous metathesis reaction was performed with Compound 3 in water. After completion of the reaction, the silica-grafted host compound was added to the reaction mixture, forming the heterogeneous host-guest compound The resulting heterogeneous solution was filtered through a cotton plug to isolate the host-guest complex containing the catalyst. The efficiency of recovery was analyzed by inductively-coupled plasma mass spectrometry (ICP-MS) of the crude reaction product, which determines the amount of residual Ru left in solution.

Figure 3:
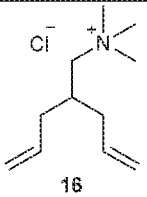
FIG. 3 is a table summarizing results of different catalyzed ring closing metathesis reactions in aqueous media. [a]Reactions were carried out at 45° C. in $D_2O$ for 24 h. Conversions were determined by $^1H$ NMR spectroscopy. [b]Analyzed by inductively-coupled plasma mass spectrometry (ICP-MS). Fully converted products 17 and 19 were characterized to measure the residual ruthenium levels. [c]90% conversion was observed with 1 mol % of catalyst 3. [d]Reactions were carried out for 48 h.
Figure 3:
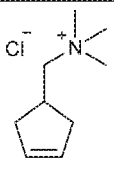
Figure 3:
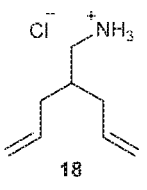
Figure 3:
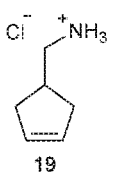
Figure 3:
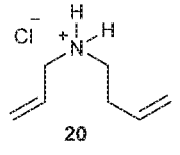
Figure 3:
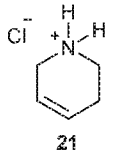
Figure 3:
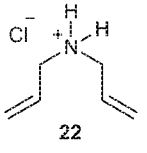
Figure 3:
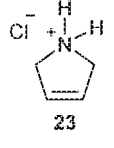

Compound 3 was used to catalyze several ring-closing metathesis (RCM) reactions of commonly used water-soluble metathesis substrates in aqueous media. The substrates are in the table in FIG. 3. Compound 3 demonstrated efficiency on par with other water soluble Ru-based olefin metathesis catalysts.

For ICP-MS analysis of RCM products, fully converted products 17 and 19 were characterized to measure the residual ruthenium levels. In order to examine the affinity of Compound 3 to unmodified silica without 13-CD (host compound), products 17 and 19 were filtered through a silica-plugged column using the same method as the host-guest recovery protocol. The products treated with unmodified silica showed significant $^1$H NMR signals corresponding to the ethylene glycol moiety of the NHC ligand. This confirmed that Compound 3 does not possess a strong affinity to unmodified silica. Also, the control test implied that the recovery of residual Ru from solution occurs via host-guest interactions.

In entry 1, quaternary ammonium salt 16 was fully converted to 17, with only 53 ppm of residual Ru (theoretical Ru level in the crude product~5,600 ppm). RCM of primary ammonium salt 18 underwent full conversion yielding compound 19 in the presence of 3 mol % Compound 3 (entry 2). The residual Ru level in this case was 284 ppm, which means that 98.7% of the total Ru was recovered by the host-guest interaction. (theoretical Ru level in crude product~22,000 ppm).

Entry 2 showed slightly lower conversion, 90%, with only 1% catalyst loading compared to 3% catalyst loading even after an extended reaction time of 48 h. Presumably, the reason is that while the nitrogen of tetraalkyl ammonium salt was highly shielded having no association to Ru metal due to alkyls, nitrogen of the primary ammonium may coordinate to the metal center after ionization in water.

RCM of two more hetero-cyclic substrates (20, 22) were tested (entries 3 and 4). Although they were moderately active compared to homocyclic substrates, the six-membered N-heterocyle 21 was more favorably formed by RCM than five-membered product 23 due to the low reactivity of catalyst as a result of the formation of Ru hydride decomposition products.

Figure 4:
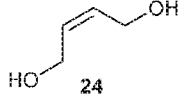
FIG. 4 is a table summarizing results of different cross metathesis reactions in aqueous media. [a]Reactions were carried out at room temperature with 5 mol % of catalyst 3 in $D_2O$ for 24 h. Conversions were determined by 1H NMR spectroscopy. [b]6% of cis-isomer remains due to thermodynamic equilibrium. [c]E/Z~8.5:1.
Figure 4:
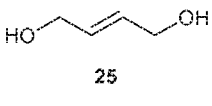
Figure 4:
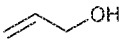
Figure 4:
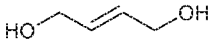

Cross metathesis of two different olefins was successfully performed in aqueous media with Compound 3 as summarized in the table of FIG. 4. The first substrate cis-2-butene-1,4-diol 24 was converted to its corresponding trans isomer 25 in 94%, while the remaining 6% resulting from thermodynamic E/Z equilibrium (entry 1). A cross metathesis reaction of allyl alcohol 26 yielded 94% of the desired metathesis product with 8.5:1 E/Z ratio (entry 2).

Figure 5:
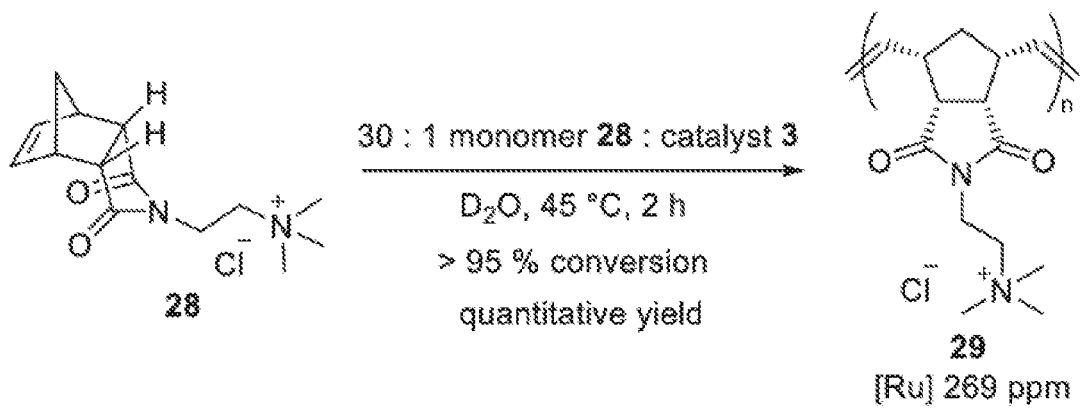
FIG. 5 is a reaction scheme of a ring opening metathesis polymerization reaction in aqueous media.

A typical olefin metathesis reaction in aqueous media was performed as follows. A dried 4 mL vial was charged with the Compound 3 (4.4 mg, 0.0020 mmol) and substrate 16 (41 mg, 0.200 mmol) in $D_2O$ 0.5 mL. The reaction mixture was stirred for 24 h at 45° C. The conversion of the crude reaction mixture was monitored by 1H NMR spectroscopy. After completion of the reaction, β-CD grafted silica 150 mg was added in the resulting solution, then stirred for 10 h at room temperature. The crude mixture was filtered on a cotton plug. The filtrate was dried in a freeze dryer. Product 17 was obtained in 80% yield (28 mg, 0.16 mmol) as a hydroscopic white solid. 1H NMR Compound 3 was also utilized to perform ROMP of norbornene monomers in water as shown in the reaction scheme in FIG. 5. The water-soluble norbornene monomer 28 was fully converted to polymer 29 in quantitative yield.

To recover the Ru catalyst with using the host-guest interaction, the reaction was quenched with 0.1 mL of ethyl vinyl ether. After quenching, the Ru catalyst was recovered from the polymer 29 by adding the inclusion compound via the host-guest interaction as described above. ICP-MS analysis showed that the final Ru content in polymer 29 was 269 ppm which represents a 97.7% recovery of Ru from solution (theoretical Ru residue amount in crude polymer product~11,500 ppm).

Because Compound 3 is homogeneously soluble in an organic solvent common to olefin metathesis, $CH_2Cl_2$, the scope of several conventional olefin metathesis substrates in $CH_2Cl_2$ (FIG. 6) was studied. The optimized reaction conditions were 1 mol % of Compound 3 at 40° C. for 1 h of reaction time followed by analysis of the crude reaction mixture with $^1$H NMR spectroscopy. The evaluated olefins—30, 32, 36, 38, and 40 demonstrated full conversion under the given conditions. Unsubstituted cyclopentenes (31, 37) were obtained at room temperature. Tetrasubstituted olefin 34 showed very low conversion due to steric congestion.

The results in the table of FIG. 6 suggest Compound 3 can be universally used in both aqueous media and organic solvent with high catalytic efficiency over a broad range of olefin substrates.

A typical olefin metathesis reaction in $CH_2Cl_2$ was performed as follows. A dried 4 mL vial was charged with Compound 3 (4.4 mg, 0.0020 mmol) and substrate 30 (48 mg, 0.200 mmol) in $CH_2Cl_2$ 0.5 mL. The reaction mixture was stirred for 1 h at room temperature. After completion of the reaction, the crude solution was diluted with diethyl ether 15 mL. The diluted solution was washed five times with water (15 mL). The organic layer was dried over $MgSO_4$.

Next, activated carbon 60 mg was added and stirred for 24 h at room temperature. After the activated carbon was filtered, the filtrate was concentrated under reduced pressure. The product 31 was obtained in 89% yield (38 mg, 0.18 mmol) as a colorless oil Phase Selective Removal of Compound 3 from Solution Compound 3 is soluble in water as well as in common organic solvents for olefin metathesis reaction such as $CH_2Cl_2$ and toluene. Compound 3 is not soluble in diethyl ether due to the presence of PEG. By leveraging this phase-selective solubility of Compound 3, the catalyst was extracted into the aqueous phase from the organic phase. This phase selective method yielded excellent recovery efficiency.

Longer PEG chains enhance the hydrophilicity of catalysts, which may lead to high recovery rates of Ru residue according to previous literature. This phase-selective recovery technique presents an alternative option for catalyst recovery when organic solvents are preferred.

This disclosure describes certain exemplary embodiments, but not all possible embodiments of the composition and methods. Where a particular feature is disclosed in the context of a particular embodiment, that feature can also be used, to the extent possible, in combination with and/or in the context of other embodiments. The composition and That which is claimed is:

1. A method comprising:
catalyzing a chemical reaction in an organic solvent using a water soluble N-heterocyclic carbene homogeneous catalyst to form a reaction mixture;
forming an aqueous phase in the reaction mixture;
adding a solvent in which the catalyst is insoluble to the reaction mixture causing the catalyst to migrate to the aqueous phase to form a catalyst-laden aqueous phase; and
extracting the catalyst-laden aqueous phase from the reaction mixture;
wherein the catalyst includes a transition metal bonded to an N-heterocyclic carbene moiety bonded to a polyethylene glycol functional group bonded to a terminal adamantyl group.

2. The method of claim 1, wherein the solvent in which the catalyst is insoluble is an ether.

3. The method of claim 1, wherein the solvent in which the catalyst is insoluble is diethyl ether.

4. The method of claim 1, wherein the chemical reaction is an olefin metathesis reaction.

5. The method of claim 1, wherein the catalyst includes the formula

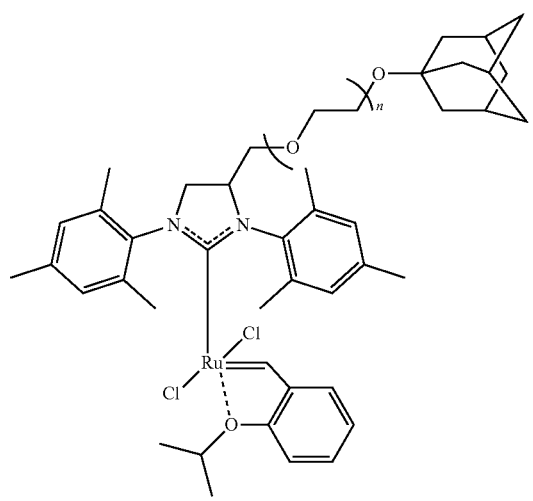

and n is the number of ethylene glycol monomers in the formula.

6. A composition comprising a water soluble homogeneous catalyst including a transition metal complex having an N-heterocyclic carbene ligand with a polyethylene glycol group thereon, further comprising a terminal adamantyl group bonded to the polyethylene glycol group.

7. The composition of claim 6, wherein the catalyst includes the formula

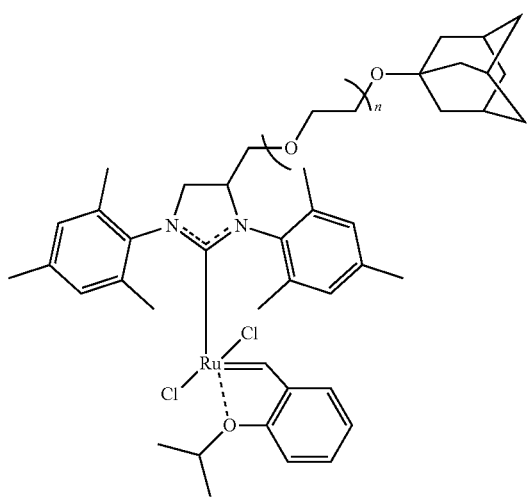

and n is the number of repeats of ethylene glycol in the formula.

8. The composition of claim 6, further comprising a cyclodextrin bound to the catalyst, the catalyst and cyclodextrin forming a host-guest compound.

9. A composition comprising a water soluble homogeneous catalyst including a transition metal complex having an N-heterocyclic carbene ligand with a polyethylene glycol group thereon, further comprising a cyclodextrin bound to the catalyst, the catalyst and cyclodextrin forming a host-guest compound.

10. The composition of claim 9, further comprising a terminal adamantyl group bonded to the polyethylene glycol group.

11. The composition of claim 9, wherein the catalyst includes the formula

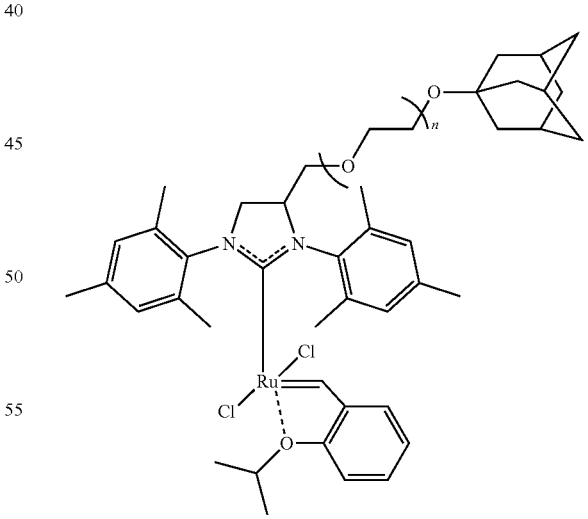

and n is the number of repeats of ethylene glycol in the formula.

12. A method comprising:
catalyzing a chemical reaction in an organic solvent using a water soluble N-heterocyclic carbene homogeneous catalyst to form a reaction mixture;

forming an aqueous phase in the reaction mixture;

adding a solvent in which the catalyst is insoluble to the reaction mixture causing the catalyst to migrate to the aqueous phase to form a catalyst-laden aqueous phase; and extracting the catalyst-laden aqueous phase from the reaction mixture using a cyclodextrin bound to the catalyst, the catalyst and cyclodextrin forming a host-guest compound.

13. The method of claim 12, wherein the catalyst includes a polyethylene glycol functional group.

14. The method of claim 12, wherein the catalyst includes a transition metal bonded to an N-heterocyclic carbene moiety bonded to a polyethylene glycol functional group.

15. The method of claim 12, wherein the catalyst includes a transition metal bonded to an N-heterocyclic carbene moiety bonded to a polyethylene glycol functional group bonded to a terminal adamantyl group.

16. The method of claim 12, wherein the catalyst includes the formula

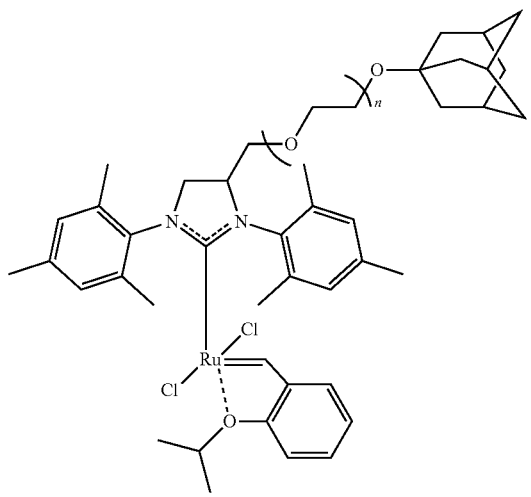

and n is the number of ethylene glycol monomers in the formula.

* * * * *